(12) United States Patent
Kahook

(10) Patent No.: US 10,561,493 B2
(45) Date of Patent: Feb. 18, 2020

(54) LENS CAPSULE TENSION DEVICES

(71) Applicant: THE REGENTS OF THE UNIVERSITY OF COLORADO, A BODY CORPORATE, Denver, CO (US)

(72) Inventor: Malik Y. Kahook, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 16/228,623

(22) Filed: Dec. 20, 2018

(65) Prior Publication Data
US 2019/0117382 A1 Apr. 25, 2019

Related U.S. Application Data

(63) Continuation-in-part of application No. 15/555,377, filed as application No. PCT/US2016/023830 on Mar. 23, 2016.

(Continued)

(51) Int. Cl.
*A61F 2/16* (2006.01)
*A61F 9/00* (2006.01)

(52) U.S. Cl.
CPC .............. *A61F 2/1694* (2013.01); *A61F 2/16* (2013.01); *A61F 2/1648* (2013.01);
(Continued)

(58) Field of Classification Search
CPC ........ A61F 2/1694; A61F 9/0017; A61F 2/16; A61F 2/1648
See application file for complete search history.

(56) References Cited

U.S. PATENT DOCUMENTS 5,275,624 A   1/1994 Hara et al.
5,843,184 A   12/1998 Cionni
(Continued)

FOREIGN PATENT DOCUMENTS

EP   0507292    7/1997
EP   1011538    2/1999
(Continued)

OTHER PUBLICATIONS

Henderson CTR, FCI Ophthalmics Products, retrieved from https://fci-ophthalmics.com/products/henderson-ctr, last viewed Apr. 11, 2019, 4 pages.

(Continued)

*Primary Examiner* — William H Matthews
(74) *Attorney, Agent, or Firm* — Morgan, Lewis & Bockius LLP

(57) ABSTRACT

The present disclosure relates generally to the fields of medical devices, ophthalmology, and cataract surgery, and more particularly to, for example, a capsular tension ring. The capsular tension ring can include an inner ring section, and an outer ring section at least partially enveloping the inner ring section. The outer ring section can have an outer ring surface, an inner ring surface, and a plurality of raised polygon features on the inner ring surface, wherein each of the raised polygon features is radially symmetric.

30 Claims, 10 Drawing Sheets

Related U.S. Application Data

(60) Provisional application No. 62/142,554, filed on Apr. 3, 2015.

(52) U.S. Cl.
CPC .... *A61F 9/0017* (2013.01); *A61F 2002/1683* (2013.01); *A61F 2210/0014* (2013.01); *A61F 2210/0057* (2013.01); *A61F 2210/0076* (2013.01)

(56) References Cited

U.S. PATENT DOCUMENTS

| | | | |
|---|---|---|---|
| 6,136,026 | A | 10/2000 | Israel |
| 6,319,282 | B1 | 11/2001 | Nishi |
| 6,413,277 | B1 | 7/2002 | Neuhann |
| 6,749,631 | B1 | 6/2004 | Pietrini et al. |
| 6,797,004 | B1 | 9/2004 | Brady et al. |
| 6,960,231 | B2 | 11/2005 | Tran |
| 6,966,913 | B2 | 11/2005 | Israel |
| 6,972,033 | B2 | 12/2005 | McNicholas |
| 6,972,034 | B2 | 12/2005 | Tran et al. |
| 7,300,464 | B2 | 11/2007 | Tran |
| 8,043,372 | B2 | 10/2011 | Bumbalough |
| 8,128,693 | B2 | 3/2012 | Tran et al. |
| 8,414,646 | B2 | 4/2013 | De Juan, Jr. et al. |
| 8,585,759 | B2 | 11/2013 | Bumbalough |
| 8,603,166 | B2 | 12/2013 | Park |
| 8,663,194 | B2 | 3/2014 | Ambati et al. |
| 8,715,346 | B2 | 5/2014 | De Juan, Jr. et al. |
| 8,728,158 | B2 | 5/2014 | Whitsett |
| 9,078,744 | B2 | 7/2015 | Van Noy |
| 9,107,748 | B2 | 8/2015 | De Juan, Jr. et al. |
| 9,339,375 | B2 | 5/2016 | Lee et al. |
| 9,757,227 | B2 | 9/2017 | Kushlin et al. |
| 2006/0235515 | A1 | 10/2006 | Chassain |
| 2007/0191941 | A1 | 8/2007 | Dick et al. |
| 2007/0010881 | A1 | 11/2007 | Soye et al. |
| 2010/0030331 | A1 | 2/2010 | Zhang et al. |
| 2010/0094415 | A1 | 4/2010 | Bumbalough |
| 2011/0160853 | A1 | 6/2011 | Scholten |
| 2011/0313521 | A1 | 12/2011 | Angelopoulos |
| 2012/0290086 | A1 | 11/2012 | Malyugin et al. |
| 2013/0304206 | A1 | 11/2013 | Pallikaris et al. |
| 2014/0172089 | A1* | 6/2014 | Lee ................... 623/6.12 |
| 2015/0094641 | A1 | 4/2015 | Park et al. |
| 2016/0030163 | A1 | 2/2016 | Akahoshi |
| 2016/0074153 | A1 | 3/2016 | Akahoshi |
| 2018/0042717 | A1 | 2/2018 | Kahook |
| 2018/0147049 | A1 | 5/2018 | Park |
| 2018/0250124 | A1 | 9/2018 | Pallikaris et al. |

FOREIGN PATENT DOCUMENTS

| | | |
|---|---|---|
| EP | 1272128 | 1/2003 |
| EP | 1581152 | 10/2005 |
| EP | 1155665 | 6/2007 |
| EP | 1653886 | 1/2008 |
| EP | 1743601 | 11/2008 |
| EP | 1809206 | 1/2009 |
| EP | 2131785 | 12/2009 |
| EP | 0884031 | 1/2013 |
| EP | 2838472 | 2/2015 |
| EP | 2341868 | 3/2015 |
| EP | 2906146 | 8/2015 |
| EP | 3277220 | 2/2018 |
| EP | 3305250 | 4/2018 |
| WO | WO-1998025652 | 6/1998 |
| WO | WO9904729 | 2/1999 |
| WO | WO0030566 | 6/2000 |
| WO | WO0164136 | 9/2001 |
| WO | WO04069101 | 8/2004 |
| WO | WO05013850 | 2/2005 |
| WO | WO06038982 | 4/2006 |
| WO | WO08108525 | 9/2008 |
| WO | WO10045294 | 4/2010 |
| WO | WO10091420 | 8/2010 |
| WO | WO2010093540 | 8/2010 |
| WO | WO11162896 | 12/2011 |
| WO | WO13158942 | 10/2013 |
| WO | WO13168141 | 11/2013 |
| WO | WO14099604 | 6/2014 |
| WO | WO16160456 | 10/2016 |
| WO | WO16195143 | 12/2016 |
| WO | WO18160800 | 9/2018 |
| WO | WO18229766 | 12/2018 |

OTHER PUBLICATIONS

Camellens Intra Ocular Lens Brochure, Soleko™, IOL Division (Italian Ophtalmic Lab), retrieved from http://www.soleko-iol.it/wp-content/materiale/schedetecniche/brochure%20Camellens-inglese.pdf, last viewed Apr. 11, 2019, 4 pages.

FDA Document, (2002) MORCHER® Capsular Tension Ring (Capsular Tension Ring-Types 14, 14A and 14C) Summary of Safety and Effectiveness Data.

FDA Document, (2004) Oculaid™ Capsular Tension Ring (Model 275 10/12 mm and Model 276 11/13 mm) summary of Safety and Effectiveness Data.

PCT International Search Report of International Application No. PCT/US2016/023830 dated Jun. 21, 2016.

* cited by examiner

Section B-B

LENS CAPSULE TENSION DEVICES

CROSS-REFERENCE TO RELATED APPLICATIONS

The present application is a continuation-in-part of U.S. application Ser. No. 15/555,377 filed on Sep. 1, 2017, which is a U.S. national stage entry under 35 U.S.C. § 371 of International Application No. PCT/US16/23830 filed on Mar. 23, 2016, which claims the benefit of priority under 35 U.S.C. § 119 of U.S. Application No. 62/142,554 filed on Apr. 3, 2015, the disclosure of each of which is hereby incorporated by reference in its entirety for all purposes.

TECHNICAL FIELD

The present disclosure relates generally to the fields of medical devices, ophthalmology, and cataract surgery.

BACKGROUND

Capsular tension rings (CTRs) are used for stabilizing the capsular bag in the eye. They are fitted as implants into the intact capsular bag and, for example after removal of the natural lens of an eye, are used to support the capsular tissue. After removal of the natural lens, for example on account of pronounced opacity, it is necessary that the opened capsular bag remains substantially in its original shape and in this way facilitates the implantation of an artificial intraocular lens (IOL). In cataract surgery, however, removal of the natural lens may result in damage to the zonular fiber tissue that secures the outside of the capsular bag in the region of its equator inside the eye. Removal of the natural lens and replacement with a substantially lower volume artificial lens also results in unpredictability of positioning of the artificial lens in the x-y-z planes. In order to avoid the associated deformations of the capsular bag or excessive stressing of the zonular fibers remaining undamaged, it is known to implant a capsular equatorial ring of the aforementioned type in the opened capsular bag. The capsular equatorial ring remains within the capsular bag during the operation and generally also after the insertion of an intraocular lens, and it presses against the tissue surrounding it in a ring shape.

BRIEF DESCRIPTION OF THE DRAWINGS

The accompanying figures, which are incorporated into and form a part of the specification, illustrate embodiments of the subject technology and, together with the description, serve to explain the principles of the subject technology. The figures are only for the purpose of illustrating aspects of the subject technology and are not to be construed as limiting.

DETAILED DESCRIPTION

I. Definitions

Figure 1:
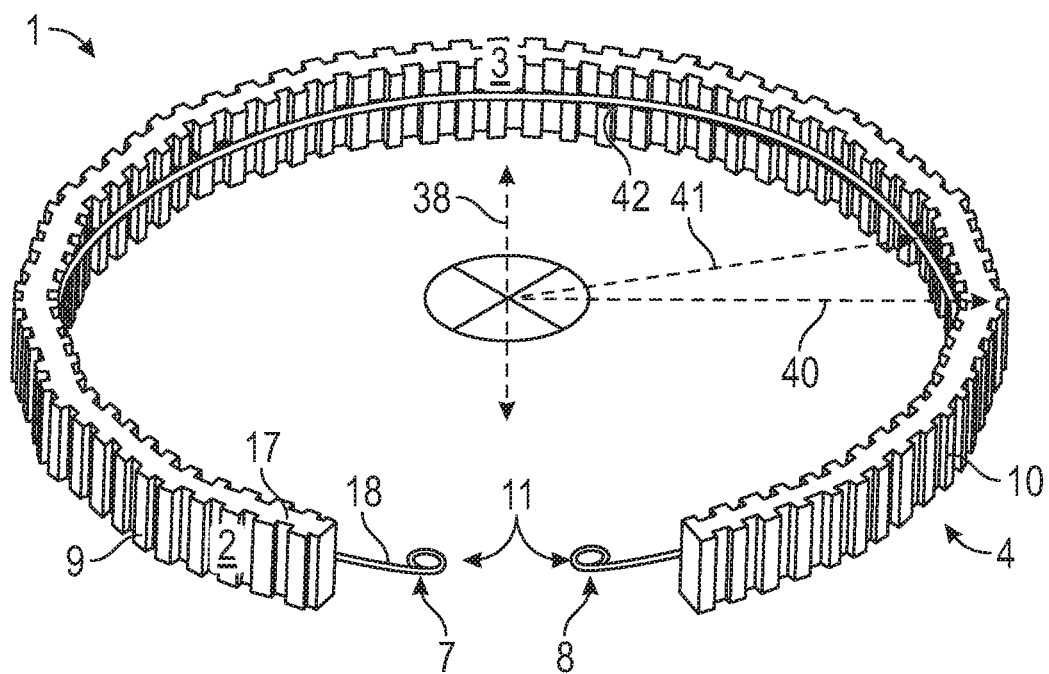
FIG. 1 is a perspective view of a capsular tension ring, according to some embodiments.

To facilitate the understanding of the subject technology, a number of terms are defined below. Terms defined herein have meanings as commonly understood by a person of ordinary skill in the areas relevant to the subject technology. Terms such as "a", "an" and "the" are not necessarily intended to refer to only a singular entity, but can include the general class of which a specific example may be used for illustration.

As used herein, the term "features" is used throughout the specification to describe patterned features, including, but not limited to polygonal features, polygonal grooves, diagonally oriented grooves, helically oriented grooves, circular grooves, intersecting grid grooves, and concentric ring grooves.

As used herein, the term "micropatterning" or "micropatterned features" preferably refers to millimeter, micrometer, and/or nanometer scale surface modifications including but not limited to laser etching, chemical etching, photo-etching, photolithography, machining, stamping, deposition processes, mechanical drilling, molding, 3D printing, Atomic Layer Deposition or other means of modifying surfaces.

As used herein, the term "overmolding" or "overmolded" is used throughout the specification to describe all molding and casting processes that can be used to overmold an underlying structure, such as the inner ring section of the device. In some embodiments, overmolding may be accomplished by an injection molding process that offers improvements in product resilience, structure, function and appearance. In some embodiments, overmolding may be accomplished by a casting process.

II. Description

Embodiments disclosed herein relate generally to the fields of ophthalmology and cataract surgery. More specifically, disclosed embodiments relate to a device that is implanted in the eye during cataract surgery and that can improve the optical functionality of the eye. Disclosed embodiments are in the field of medical devices and relate to capsular tension rings that are designed to be implanted in the capsular bag after removal of the crystalline lens affected by a cataract in association with an intraocular lens designed to replace the crystalline lens. Some embodiments apply to stabilizing an implanted artificial lens from movement in the x-y-z planes and preventing undesired rotation.

According to some embodiments, a device comprises an open capsular tension ring comprising an inner ring surface and an outer ring surface, said inner and outer ring surfaces populated with a series of raised parallel polygon features, wherein each of said polygon features comprise at least one distinct edge. In some embodiments, at least one distinct edge is a sharp edge. In some embodiments, at least one distinct edge is a curved edge. In some embodiments, said ring further comprises a first end and a second end. In some embodiments, said ring further comprises a first arcuate arm extending from said first end. In some embodiments, said ring further comprises a second arcuate arm extending from said second end. In some embodiments, said first arcuate arm further comprises a first eyelet. In some embodiments, said second arcuate arm further comprises a second eyelet. In some embodiments, said first and second eyelets are coplanar. In some embodiments, said first arcuate arm and said second arcuate arm are coplanar. In some embodiments, said features protrude from the inner and outer surfaces of the ring towards the center and away from the geometric center of the ring. In one embodiment, said features protrude from the inner and outer planes of the ring towards the center and away from the geometric center of the ring. In some embodiments, said outer surface further comprises vertical features. In some embodiments, said inner surface further comprises vertical features. In some embodiments, said outer surface further comprises horizontal features. In some embodiments, said inner surface further comprises horizontal features. In some embodiments, said features can be coupled with opposing features on an interfacing device to stabilize said interfacing device. In some embodiments, said interfacing device is an intraocular lens implant or lens haptic implant. In some embodiments, said stabilizing comprises rotational resistance. Some embodiments apply to stabilizing the artificial lens from movement in the x-y-z planes. In some embodiments, said features are etched. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL that corrects astigmatism). In some embodiments, said ring comprises polymer and material content that allows for optical coherence topography imaging (allows for anterior segment OCT visualization and targeting). In some embodiments, the features that are micropatterned also have adhesive and/or cohesive qualities. In some embodiments, the inner and outer surface of the ring has adhesive and/or cohesive qualities without micropatterns or etching. In some embodiments, said ring contains at least one medication. In some embodiments, said medication is selected from the group comprising anti-fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelia, matrix-metalloproteinase inhibitors, CNPA, corticosteroids, and/or antibody-based immunosuppressants. In some embodiments, said medication is combined with a silicone material. In some embodiments, said medication is combined with a polymer. In some embodiments, said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), poly(vinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In some embodiments, said outer surface slowly releases medication.

According to some embodiments, a method comprises: a) providing; i) an insertion device; and ii) a capsular tension ring comprising an inner ring surface and an outer ring surface, said inner and outer ring surfaces populated with a series of raised parallel polygon features, wherein each of said polygon features comprise at least one distinct edge, and b) applying outward pressure to an equatorial region of said capsular tension ring with said insertion device wherein said capsular tension ring is inserted into an ocular lens capsule.

According to some embodiments, a method comprises: a) providing; i) an insertion device; and ii) a capsular tension ring comprising an inner ring surface and an outer ring surface, said inner and outer ring surfaces populated with a series of raised parallel polygon features, wherein each of said polygon features comprise at least one distinct edge; b) loading of said capsular tension ring into said insertion device; and c) inserting said capsular tension ring into an ocular lens capsule. In some embodiments, at least one distinct edge is a sharp edge. In some embodiments, at least one distinct edge is a curved edge. In some embodiments, said capsular tension ring further comprises a central fixation element attached to said insertion device. In some embodiments, said central fixation element comprises two oppositely extending arcuate arms that engage along an equatorial region of said capsular tension ring. Some embodiments apply to stabilizing the artificial lens from movement in the x-y-z planes. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL, that corrects astigmatism). In some embodiments, said ring comprises polymer and material content that allows for optical coherence topography imaging (allows for anterior segment OCT visualization and targeting). In some embodiments, the features that are micropatterned also have adhesive and/or cohesive qualities. In some embodiments, the inner and outer surface of the ring has adhesive and/or cohesive qualities without micropatterns or etching. In some embodiments, said ring contains at least one medication. In some embodiments, said medication is selected from the group comprising antifibrotic agent, anti-inflammatory agent, immunosuppressant agent, anti-neoplastic agent, migration inhibitors, anti-proliferative agent, rapamycin, triamcinolone acetonide, everolitnus, tacrolimus, paclitaxel, actinomycin, azathioprine, dexamethasone, cyclosporine, bevacizumab, an anti-VEOF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrixmetalloproteinase inhibitors, CNPA, corticosteroids, and/or antibody-based immunosuppresants. In some embodiments, said medication is combined with a silicone material. In some embodiments, said medication is combined with a polymer. In some embodiments, wherein said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), polyvinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In some embodiments, said outer section slowly releases medication.

According to some embodiments, a method comprises: a) providing: i) a capsular tension ring comprising an inner ring surface and an outer ring surface, said inner and outer ring surfaces populated with a series of raised parallel polygon features, wherein each of said polygon features comprise at least one distinct edge; and ii) an elongated fixation element attached to said capsular tension ring, said fixation element having a first end fixed to said capsular tension ring and a second free end; b) implanting said capsular tension ring in an ocular capsular bag between the posterior capsule and the annular anterior capsular flap with said elongated fixation element. In some embodiments, at least one distinct edge is a sharp edge. In some embodiments, at least one distinct edge is a curved edge. In some embodiments, said implanting comprises positioning said fixation element having a first end fixed to said capsular tension ring and a second end extending past an capsulorhexis edge and positioned anterior to said ocular capsular bag with an annular anterior capsular flap positioned therebetween. In some embodiments, the method further comprises the step of attaching said second free end of said fixation element to an ocular scleral wall, whereby said capsular tension ring generally stabilizes and centralizes said capsular bag in an ocular posterior chamber. Some embodiments apply to stabilizing the artificial lens from movement in the x-y-z planes. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL that corrects astigmatism). In some embodiments, said ring comprises polymer and material content that allows for optical coherence topography imaging (allows for anterior segment OCT visualization and targeting). In some embodiments, said ring contains at least one medication. In some embodiments, said medication is selected from the group comprising antifibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrixmetalloproteinase inhibitors, CNPA, corticosteroids, and/or antibody-based immunosuppresants. In some embodiments, said medication is combined with a silicone material. In some embodiments, said medication is combined with a polymer. In some embodiments, wherein said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), poly(vinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In some embodiments, said outer section slowly releases medication.

According to some embodiments, a capsular tension ring for insertion into an ocular lens capsule to apply outward pressure in the area of the equatorial region comprises an inner ring section and an outer ring section, said inner ring section having: a central fixation element; two arcuate arms extending generally oppositely from the fixation element, said arms forming an arc to engage along the equatorial region of the capsule, said fixation element and arms being constructed; and outer section enveloping said inner ring section. In some embodiments, said outer section having: a vertical profile of at least 1.0 millimeters and horizontal profile of at least 150 micrometers. In some embodiments, the capsular tension ring further comprises an inner ring surface and an outer ring surface, said inner and outer ring surfaces populated with a series of raised parallel polygon features, wherein each of said polygon features comprise at least one distinct edge. In some embodiments, at least one distinct edge is a sharp edge. In some embodiments, at least one distinct edge is a curved edge. In some embodiments, said central fixation element is configured to be received by an insertion device. In some embodiments, said capsular tension ring arm is arranged relatively to be loaded into the insertion device by pulling on the central fixation element and thereby draw the arms into the insertion device together, followed by discharge of the arcuate arms together from the device into the capsule. In some embodiments, said fixation element and the aims are coplanar. In some embodiments, said ring further includes a stem section between the fixation element and the arms. In some embodiments, said arms are coplanar and the fixation element is offset out of the plane of the arms when deployed in a capsule. In some embodiments, said fixation element is an eyelet. In some embodiments, said fixation element is a groove formed between adjacent ends of the arms. In some embodiments, said inner section is made from nitinol. In some embodiments, said outer section is made from polymer materials that allows for absorption or incorporation of drugs for slow release. In some embodiments, said outer section is overmolded upon said inner section. In some embodiments, said outer section has a distinct sharp edge. In some embodiments, said outer section has vertical features. In some embodiments, said outer section vertical features comprise outer ring surface vertical features. In some embodiments, said outer section vertical features comprise inner ring surface vertical features. In some embodiments, said ring provides rotational stability to the subsequently implanted intraocular lens. Some embodiments apply to stabilizing the artificial lens from movement in the x-y-z planes. In some embodiments, said features are produced by etching. In some embodiments, said features are micropatterned features. In some embodiments, said features are configured as interlocking features. In some embodiments, said features are configured as docking and receiving features. In some embodiments, said features are magnetic. In some embodiments, said features are markings to identify dock hour relative to ocular surface features (helps with implantation of the IOL that corrects astigmatism. In some embodiments, said ring comprises polymer and material content that allows for optical coherence topography imaging (allows for anterior segment OCT visualization and targeting). In some embodiments, said ring contains at least one medication. In some embodiments, said medication is selected from the group comprising and—fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-I agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrix-metalloproteinase inhibitors, CNPA, corticosteroids, and/or antibody-based immunosuppressants. In some embodiments, said medication is combined with a silicone material. In some embodiments, said medication is combined with a polymer. In some embodiments, said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), polyvinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In some embodiments, said outer section slowly releases medication.

According to some embodiments, a device for restoring and maintaining the natural tension and anatomy of a lens capsule post-surgically in an eye of a subject comprises: an open capsular tension ring structure having a shape configured to circumferentially fit within a post-surgical lens capsule of the eye. Some embodiments apply to stabilizing the artificial lens from movement in the x-y-z planes. In some embodiments, the capsular tension ring structure may have a shape formed to circumferentially contact an inner surface of the lens capsule. In addition, the shape of the capsular tension ring structure is substantially that of a natural lens peripheral shape. Furthermore, natural elasticity of the lens capsule may circumferentially anchor the open capsular tension ring structure continuously to an internal capsular surface. In some embodiments, the device is secured in place by the raised features of the outer ring surface or outer ring surface of the outer section of the ring. Further still the open capsular tension ring structure may comprise an elastic material, such as silicone, acrylic or other materials used for the production of foldable IOLs or materials effective as drug delivery vehicles.

According to some embodiments, a method for restoring natural tension and anatomy of a lens capsule post-surgically in an eye of a subject comprises the steps of anchoring the device, such as with the eyelets on each end of the device, circumferentially to an internal surface of the lens capsule of the post-surgical eye; and providing tension to an equatorial area of the lens capsule via the capsular tension ring structure comprising the device whereby the capsular tension ring structure directs tension inwardly towards the center of the lens capsule such that an equatorial diameter of the lens capsule is decreased, thereby restoring natural tension and anatomy to the lens capsule. In some embodiments, the vertical features on the outside surface of the device anchor the capsular tension ring structure in place and prevents undesired rotation of the ring or any device attached to said ring. In some embodiments, the variable horizontal width of the raised features prevents rotation and provides an anchoring feature. In some embodiments, the variable vertical height of the outer section prevents rotation and provides an anchoring feature.

According to some embodiments, a method for restoring natural tension and anatomy of a lens capsule post-surgically in an eye of a subject comprises the steps of inserting the open capsular tension ring device, as described supra, circumferentially into an internal surface of the lens capsule of the post-surgical eye wherein the raised features articulate into a space around the lens capsule, said raised features disposed proximately to an equatorial area of the lens capsule whereby the natural tension and anatomy of the lens capsule in the eye is restored. Some embodiments apply to stabilizing the artificial lens from movement in the x-y-z planes.

III. Use of the Device

Generally, the following indications may exist for implanting a capsular tension ring in the capsular bag; local absence of zonular fibers, or damaged zonular fibers, guarantee of consistent operating conditions, luxation of an IOL, desired extension or spreading of the capsular bag, stabilization of the capsular bag after removal of the lens in cases of high myopia, zonulolysis, pseudoexfoliation, Marchesani syndrome, and simplified implantation of foldable intraocular lenses. Some embodiments have the additional aspects of stabilizing a connected intraocular lens in the x-y-z dimension and also inhibiting PCO by providing a distinct upper and lower edge to the device for prevention of central migration of epithelial cells in the lens bag.

Moreover, according to some embodiments, the implantation of the capsular tension ring affords one or more of the following advantages: circular spreading of the capsular bag, consistent operating conditions, prevention of secondary cataract, inhibition of capsular bag shrinkage, minimizing or avoidance of capsular bag folds, reduced clouding of the anterior capsule margin and thus better fundus visualization, e.g. in patients with problems affecting the retina.

Among other things, provided herein are devices, systems and methods for restoring natural capsular tension and anatomy post-surgically in the lens capsule of an eye. The capsular tension ring can be implemented as an open capsular tension ring device that is anchorable in the lens capsule of the eye after lens extraction, such as during cataract surgery. The open capsular tension ring device can anchor to the peripheral part of the internal capsular surface, or can be anchored by the natural capsular structure of the lens capsule. The outer section of the open capsular tension ring device may comprise an elastic material and/or may be a material effective for delivery of a drug, pharmaceutical or other therapeutic compound as is known in the art. The inner section of the open capsular tension ring device may comprise a stiff central open ring. In some embodiments, said inner section comprises a plastic or metal material, such as nitinol. For example, the outer section of the open capsular tension ring device may comprise a plastic, silicone, acrylic, or other material useful for the production of a flexible intraocular lens. The device may be coupled to an appropriate opto-mechanical mechanism to perform accommodation.

The device may be coupled with an ophthalmic lens system, such as an intraocular lens with mounting structures. The device may be designed, formed or configured to receive an intraocular lens while anchored to the lens capsule. Optionally the intraocular lens may add to or solely provide the inwardly directed tension to reduce the capsular equatorial diameter upon incorporation into the tensioning device. Thus, some embodiments also provide a method of restoring capsular tension to a post-surgical eye via implantation of the device or ophthalmic lens system into the post-surgical lens capsule and to stabilize an implanted artificial lens from movement in the x-y-z planes.

The described aspects, structures, or characteristics of the subject technology may be combined in any suitable manner in one or more embodiments. In the following description, numerous specific details are recited to provide a thorough understanding of embodiments of the subject technology. One skilled in the relevant art may recognize, however, that the subject technology may be practiced without one or more of the specific details, or with other methods, components, materials, and so forth. In other instances, well-known structures, materials, or operations are not shown or described in detail to avoid obscuring aspects of the subject technology.

Other objects, advantages, and novel features, and further scope of applicability of the present technology will be set forth in part in the detailed description to follow, taken in conjunction with the accompanying drawings, and in part will become apparent to those skilled in the art upon examination of the following, or may be learned by practice of the technology. The objects and advantages of the subject technology may be realized and attained by means of the instrumentalities and combinations particularly pointed out in the appended claims.

IV. Device Description

Embodiments disclosed herein comprise a CTR. CTRs are generally used in cataract surgery. Cataract surgery can involve removing a cataractous lens and implanting an artificial lens implant for vision correction. The lens bag that receives the IOL implant can be compromised due to laxity of supporting fibers (called zonules) and may require support with a tensioning ring that is inserted prior to insertion of the IOL. Capsular tension rings are these tensioning rings.

According to some embodiments, the CTR can have a larger vertical (e.g., 1.5 millimeters) and horizontal (e.g., 500 micrometers) body profile. This may, for example, address the poor ability of current devices to place the capsular bag on stretch to provide for more predictable positioning of the IOL implant and the inability to separate the anterior and posterior capsule which results in posterior capsular opacification (PCO) and anterior capsular opacification (ACO) and subsequent IOL decentration.

According to some embodiments, the CTR can be manufactured from polymer materials (e.g., silicone or other) that allow for absorption or incorporation of drugs for slow release compared to CTRs that are made of poly(methyl methacrylate) (PMMA).

According to some embodiments, the CTR can have a distinct edge design that allows for prevention of PCO. In some embodiments, said distinct edge is sharp or curved. In some embodiments, the vertical features on the sides are ~200 micrometers wide and 200 micrometers in between each features. In some embodiments, said features are produced by etching.

According to some embodiments, the CTR can have one or more eyelets at one or more ends of the CTR, which can, for example, permit anchoring or fixation of the CTR device. According to some embodiments, the eyelet(s) can be radially overlapped by the outer section of the device. This can, for example, facilitate insertion of the CTR into a CTR injector device, or increase an ease of insertion of the CTR into the CTR injector device, by reducing a tendency of portions of the CTR such as the outer section to catch on components of the CTR injector device upon loading of the CTR into the injector device.

According to some embodiments, the CTR may be designed having an inner surface and outer surface, either or both of which can be populated with polygons having multiple surface features. In some embodiments, said features are micropatterned features. In some embodiments, these features function to provide to the capsular bag with enhanced stability (anti-rotation ability). In some embodiments, the surface features may be designed to receive IOL haptics and act as a rotational braking system to prevent or otherwise reduce undesired post-operative clockwise or counterclockwise rotation of an implanted lens. This may lead to the success of "toric" lenses that are designed to correct vision (astigmatism) with different powers in different lens meridians. As they exist today, these lenses rotate significantly and can lead to suboptimal vision correction. A rotational braking system on a CTR would allow for enhanced vision restoration and stability of astigmatism correction over the long-term. According to some embodiments, the features of the rotational braking system may additionally permit bi-directional rotation of the IOL device (in both clockwise and counter-clockwise directions) upon application of an external force during a surgical implantation procedure. This can, for example, allow for precise rotational positioning of a toric lens by a surgeon.

According to some embodiments, the CTR may contain features to help guide positioning of a secondary device, such as an IOL haptic. In some embodiments, said features are structural features on the surface of the ring. In some embodiments, said features are configured as interlocking features. In some embodiments, said features are configured as docking and receiving features. In some embodiments the receiving/docking features are married to receiving/docking features on an IOL or IOL haptic. In some embodiments, said features are micropatterned features. In some embodiments, said features are magnetic.

According to some embodiments, the CTR can have markings to identify clock hour (rotational position) relative to ocular surface features (e.g., to help with implantation of the IOL that corrects astigmatism).

According to some embodiments, the CTR can have polymer and material content that allows for optical coherence topography (OCT) imaging (e.g., to allow for anterior segment OCT visualization and targeting).

According to some embodiments, the CTR can be coated with secondary materials to slow exit of drug that is incorporated into body of CTR. In some embodiments, the drug is incorporated into the outer section of the device.

FIGS. 1-18 show a capsular tension ring 1 and components associated with such a ring, in accordance with some embodiments.

With reference to, for example, FIG. 1, the capsular tension ring 1 can be implemented as an open capsular tension ring that is generally C-shaped. The capsular tension ring 1 has an outer surface 2 and an inner surface 3. The outer surface 2 and inner surface 3 are each annular surfaces or ring surfaces that extend about a central axis 38 which forms a geometric center of the ring. The outer surface 2 extends along an outer circumference and corresponds to an outer radius 40 of the capsular tension ring 1. The inner surface 3 extends along an inner circumference and corresponds to an inner radius 41 of the capsular tension ring 1.

The capsular tension ring 1 has features 4 on both the outer surface 2 and the inner surface 3. The features 4 are arranged circumferentially along the outer surface 2 and inner surface 3. Although features 4 are shown arranged on both the outer surface 2 and inner surface 3, implementations are contemplated in which the capsular tension ring 1 has such features on only the outer surface 2 or inner surface 3.

With continued reference to, for example, FIG. 1, the capsular tension ring 1 has a first end 7 and second end 8 each with an eyelet 11. In this particular embodiment, the ring also has an inner section 18 and an outer section 17. In some embodiments, the inner section 18 is made from a wire and the outer section 17 is made from a material molded or deposited over the inner section 18 wire. The features 4 are formed at least in part on the surface or surfaces of the outer section 17. The inner section 18 has a generally annular or arcuate portion 42 extending from the first end 7 to the second end 8 with a curved configuration about central axis 38. The capsular tension ring 1 is symmetrical with two arcuate arms, a first arcuate arm 9 and a second arcuate arm 10.

Figure 2:
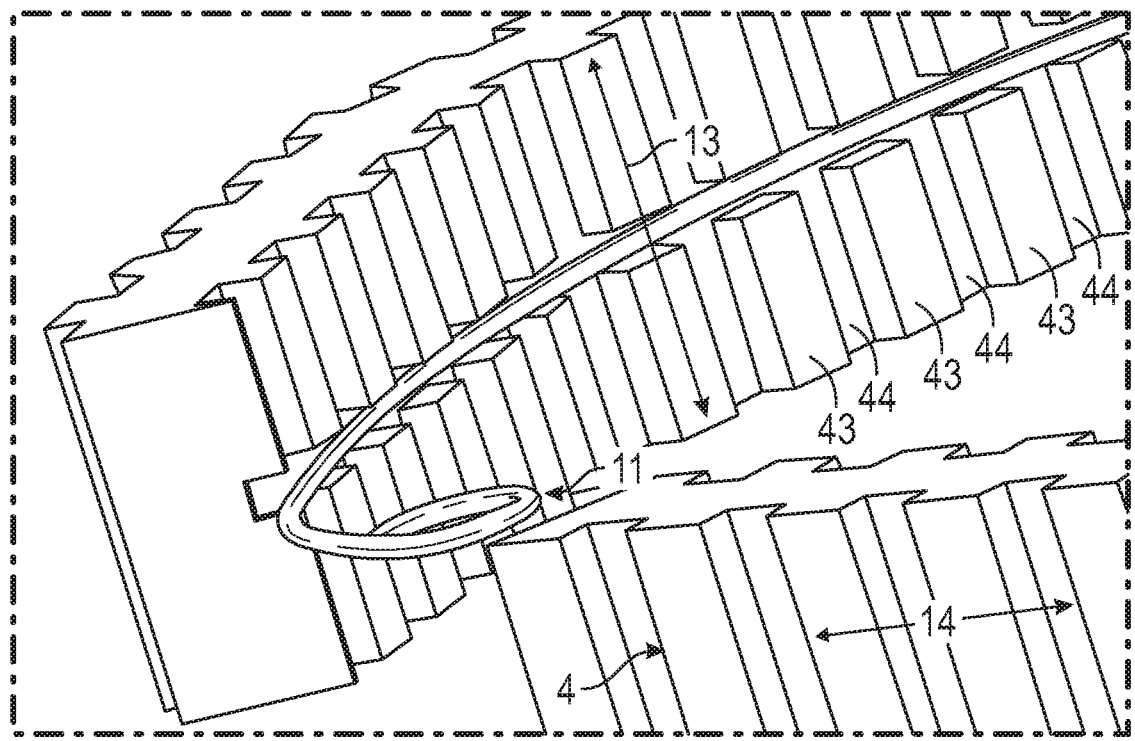
FIG. 2 is an enlarged view of an end of a capsular tension ring, according to some embodiments.

FIG. 2 shows a close up of one of the ends of the capsular tension ring 1. Vertical features 13 extend in an axial direction along the direction of central axis 38 and may vary in width in the axial direction, indicated by the arrow. Alternatively, they may have constant width in some embodiments. Horizontal features 14 extend in a circumferential direction along a circumference of the capsular tension ring 1 (e.g., outer or inner circumference) and are also indicated with the arrows.

The features 4 are shown in FIG. 2 as raised parallel polygon features forming a series of ridges 43 and valleys 44. The polygon features are referred to as parallel in that each polygon feature can be parallel to its adjacent polygon features, thereby forming a series of parallel ridges and valleys. In the illustrated example, the polygon features extend substantially straight in the axial direction (direction along central axis 38), although they can alternatively be angled with respect to the central axis 38 (e.g., similar to the teeth of a helical gear), or have curved geometries in the axial direction (e.g., similar to the teeth of a screw gear). In curved geometry implementations, the polygon features may extend along parallel curves to each other, for example.

Figure 3:
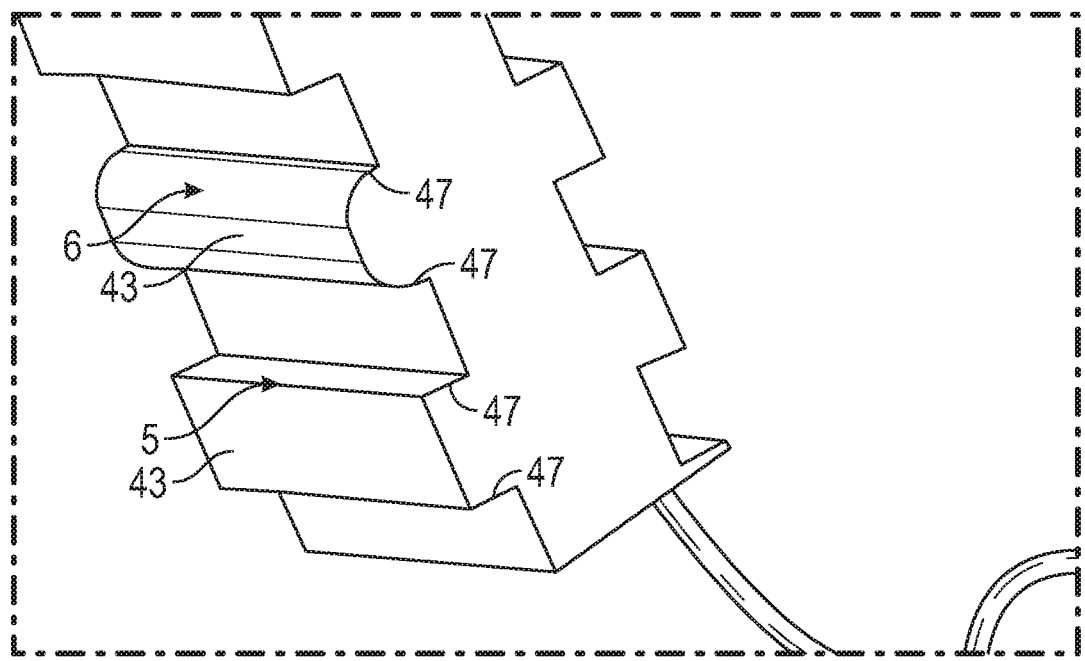
FIG. 3 is an enlarged view of features on a capsular tension ring, according to some embodiments.

FIG. 3 shows a close up of features 4 implemented as raised parallel polygon features. In some embodiments, the raised parallel polygon features have a sharp edge 5, and in some embodiments, the features have a curved edge 6. In some embodiments, the capsular tension ring 1 can include both sharp edges 5 and curved edges 6.

As seen in FIG. 3, for example, a ridge 43 having a sharp edge 5 can have opposing sides 47 that extend substantially parallel to each other in a radial direction, and a ridge 43 having a curved edge 6 can have opposing sides 47 that converge towards each other in a radial direction. For ridges 43 having curved edge 6 that protrude radially outward from the outer surface 2, the opposing sides 47 can converge towards each other in a direction away from the central axis 38. For ridges 43 having curved edge 6 that protrude radially inward from the inner surface 3, the opposing sides 47 can converge towards each other in a direction towards from the central axis 38.

Figure 4:
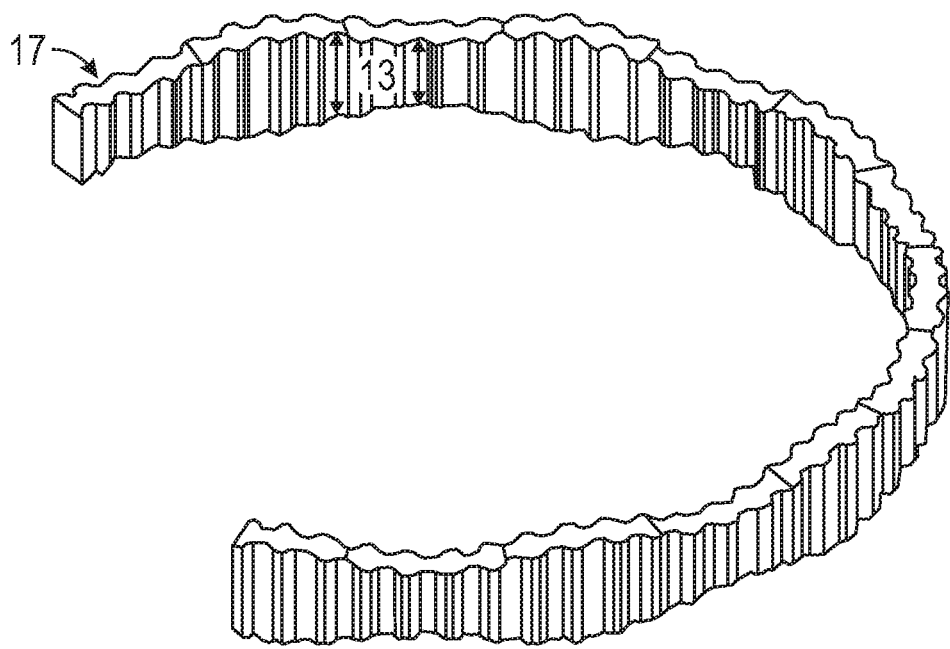
FIG. 4 is a perspective view of an outer section of a capsular tension ring, according to some embodiments.

FIG. 4 shows a view of the outer section 17 of the capsular tension ring 1. This figure shows the variability of the vertical features 13. The height may vary in addition to the variability of the horizontal features 14. In some embodiments, the outer section 17 is comprised of polygonal sections, which may vary in vertical, horizontal, or both vertical and horizontal widths. As seen in FIG. 4, the variability can result in wavy upper and/or lower borders. It is also contemplated that any one or more of the forgoing aspects can be made constant as opposed to varying. For example, FIG. 1 shows the outer section 17 implemented with substantially constant vertical width resulting in substantially flat upper and lower borders. The vertical dimension in this case can alternatively be referred to as the axial direction as it extends along the direction of central axis 38 or the axis of the ring.

Figure 5:
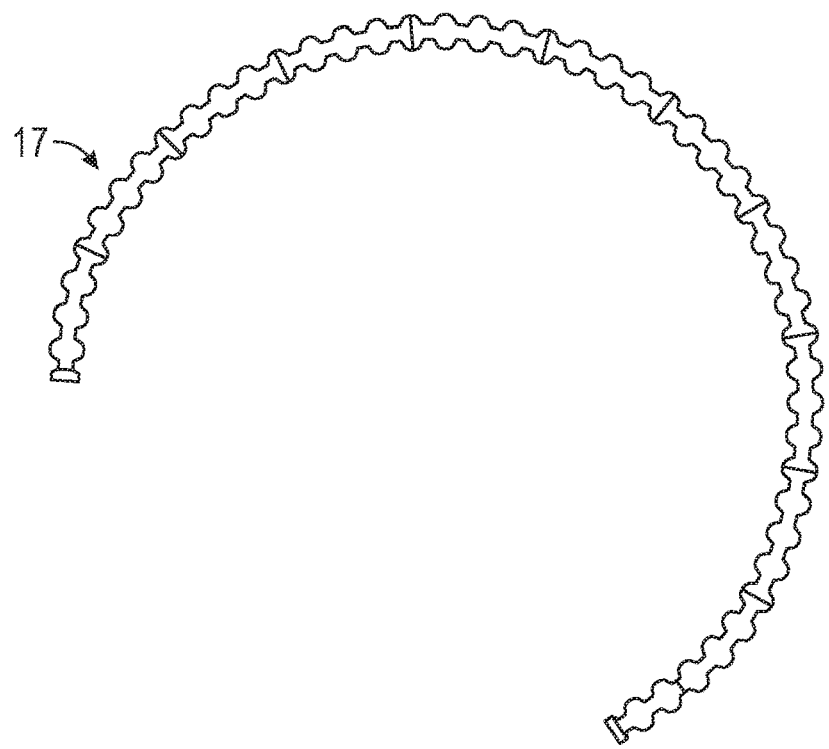
FIG. 5 is a plan view of an outer section of a capsular tension ring, according to some embodiments.
Figure 6:
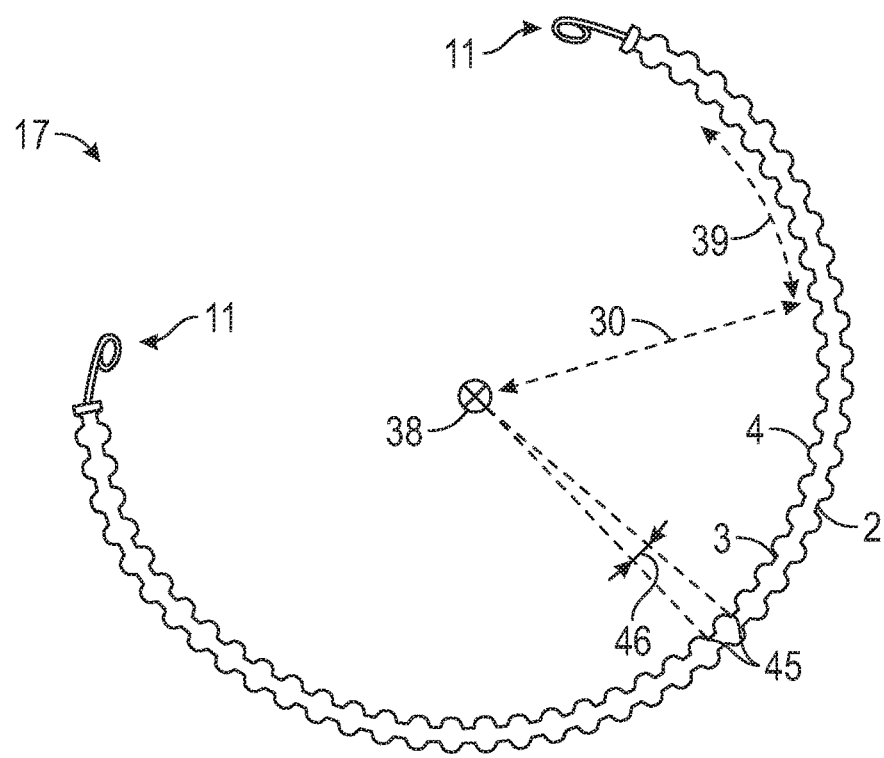
FIG. 6 is a plan view of a capsular tension ring, according to some embodiments.

FIG. 5 shows an overhead view of the outer section 17 of the capsular tension ring 1. FIG. 6 shows an underside view of the outer section 17 of the capsular tension ring 1 with the ends of the inner section 18 emerging from the ends of the outer section 17. Eyelets 11 are disposed at the ends of the inner wire section 18 and emerge from the ends of the outer section 17 so that they are exposed outside of the outer section 17.

FIG. 6 also shows an example of how features 4 can be arranged circumferentially along the inner surface 3 and/or outer surface 2, so that the features 4 can have a pattern such as a ridge and valley pattern or other repeating structure that repeats in the circumferential direction 39 about central axis 38. As seen in FIG. 6, the features 4 can include protrusions (e.g., ridges or raised polygon structures) on the inner surface 3 that protrude radially inward from inner surface 3, or toward central axis 38 in radial direction 30. As seen in FIG. 6, the features 4 can include protrusions (e.g., ridges or raised polygon structures) on the outer surface 2 that protrude radially outward from outer surface 2, or away from central axis 38 in radial direction 30.

According to some embodiments, a solid angle 46 subtended from the central axis 38 by an adjacent pair 45 of features 4 such as an adjacent pair of ridges can provide a stepwise rotational positioning system for an intraocular lens or other interfacing device to slide along the inner surface 3 upon application of external force to the interfacing device (e.g., by a surgeon). For example, upon application of the external force, the interfacing device may be able to stepwise click into place as it slides from ridge to ridge, while in the absence of the external force, the ridges can resist rotation of the interfacing device to provide a rotational braking system. The solid angle 46 can vary depending the implementation, and factors such as manufacturing processes, construction of the features 4, or desired rotational precision for the interfacing device. According to some embodiments, for example, the solid angle 46 can be less than 10 degrees. According to some embodiments, for example, the solid angle 46 can be less than 5 degrees. According to some embodiments, for example, the solid angle 46 can be less than 3 degrees. According to some embodiments, for example, the solid angle 46 can be between 10 degrees and 0.5 degrees. According to some embodiments, for example, the solid angle 46 can be between 5 degrees and 0.5 degrees. According to some embodiments, for example, the solid angle 46 can be between 3 degrees and 0.5 degrees. It is also contemplated that the solid angle can be outside of these ranges, for example.

Figure 7:
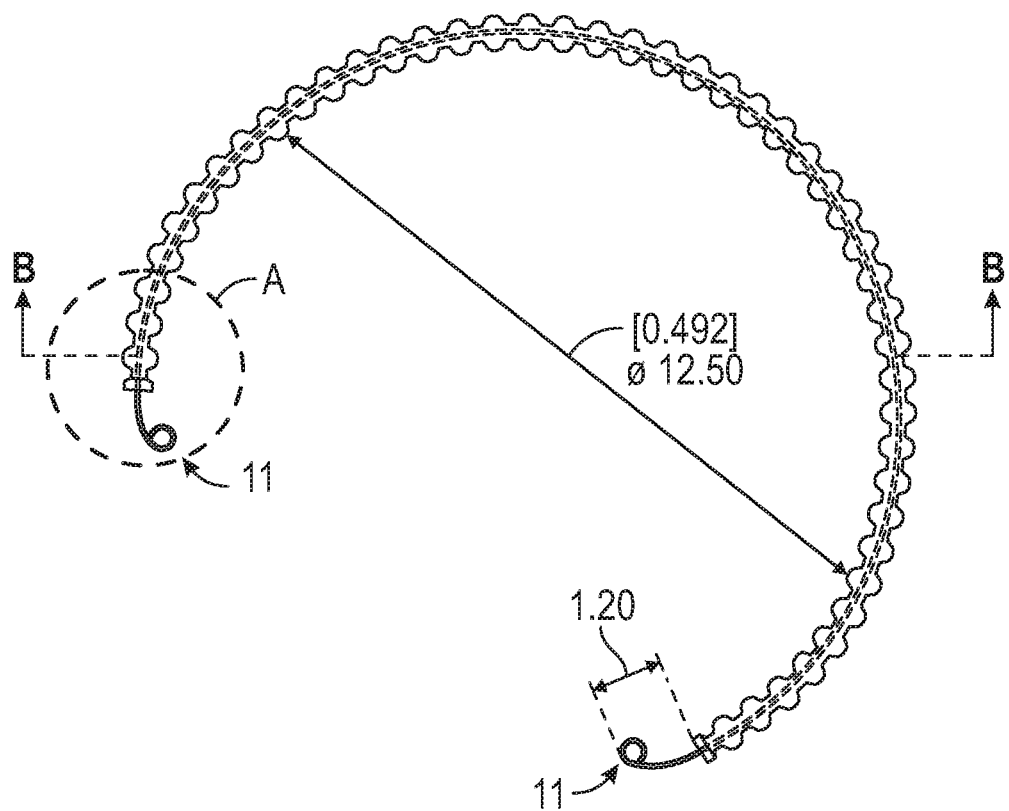
FIG. 7 is a plan view of a capsular tension ring, according to some embodiments.

FIG. 7 shows an overhead view of the outer section 17 of the capsular tension ring 1 with the ends of the inner section 18 emerging from the ends of the outer section 17. Eyelets 11 at the ends of the inner wire section 18 emerge from the ends of the outer section 17 from the eyelet holes 12, encircled next to B and shown in greater detail in FIGS. 8 and 11. In this embodiment, the inner section 18 has been overmolded to form an outer section 17. FIG. 7 also shows examples of dimensions that can be employed in the capsular tension ring 1.

Figure 8:
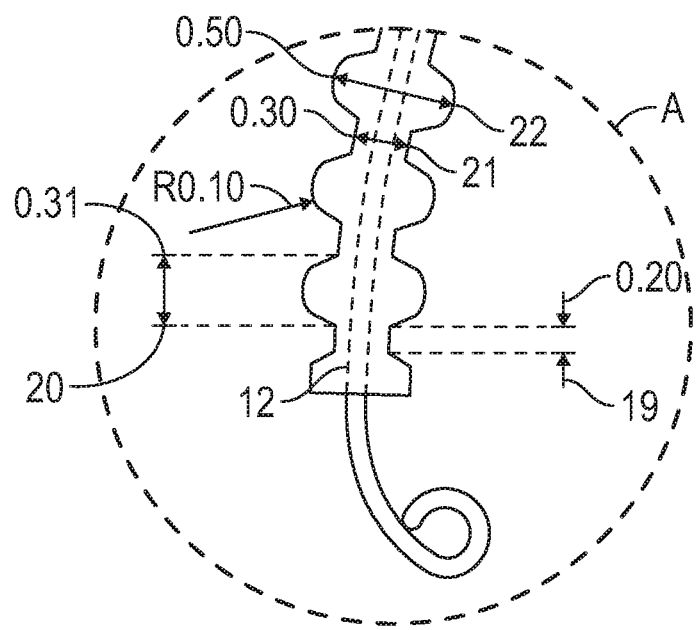
FIG. 8 is an enlarged view of an end of a capsular tension ring, according to some embodiments.

FIG. 8 shows a detailed view of the end of the capsular tension ring 1. In this particular example, there is a 0.20 millimeter horizontal width at the bottom 19 of the raised parallel polygonal features. This value is equivalent to the width of valleys in the circumferential direction 39. The raised polygonal features (which can have curved 6 and sharp edges 5) have a width 20 of 0.31 millimeter distance. This value is equivalent to the width of ridges in the circumferential direction 39. In this example, the outer section 17 has a width of 0.30 millimeters at the thinnest section 21 and 0.50 millimeters at the greatest width 22. These values are equivalent to the thickness of the outer section 17 in the radial direction 30. It will be appreciated that these are just some examples of dimensions that can be employed in the capsular tension ring 1, and it is contemplated that numerous other dimensions can be employed.

Figure 9:
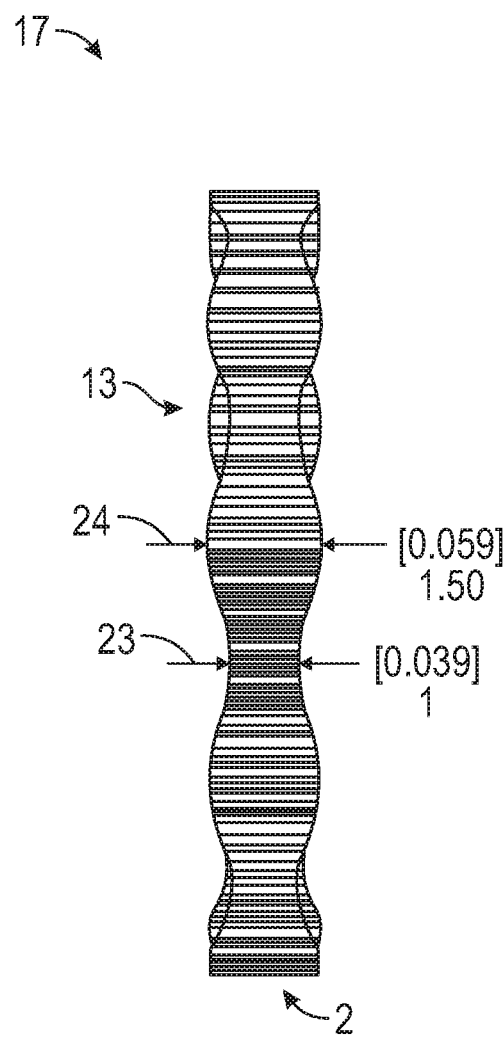
FIG. 9 is a side view of a capsular tension ring, according to some embodiments.

FIG. 9 shows a side view of the vertical features 13 of the outer section 17 and outer surface 2 of the capsular tension ring 1. The smallest vertical height 23 of the outer section vertical features has a width of 1.0 millimeter. The largest vertical height 24 of the outer section vertical features has a width of 1.5 millimeters. These values are equivalent to the thickness of the outer section 17 along a direction of the axis 38. It will be appreciated that these are just some examples of dimensions that can be employed in the capsular tension ring 1, and it is contemplated that numerous other dimensions can be employed, including constant vertical heights or thickness in the axial direction.

Figure 10:
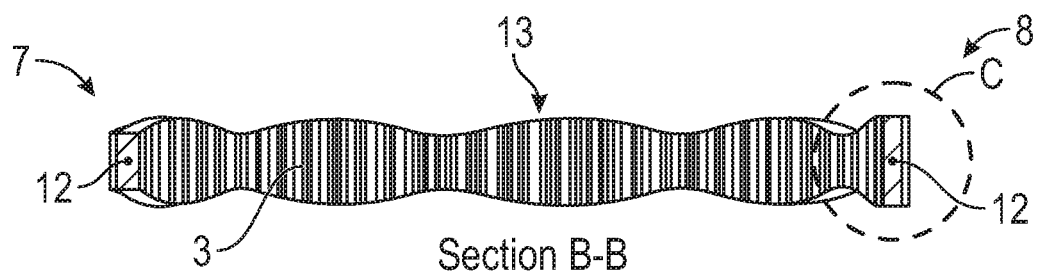
FIG. 10 is a front view of a capsular tension ring, according to some embodiments.

FIG. 10 shows a side view of the vertical features 13 of the outer section 17 and inner surface 3 of the capsular tension ring 1. The first end 7 and second end 8 are visible with the eyelet holes 12 at the ends. A detailed view of the second end 8 is shown encircled in detail C, see FIG. 11.

Figure 11:
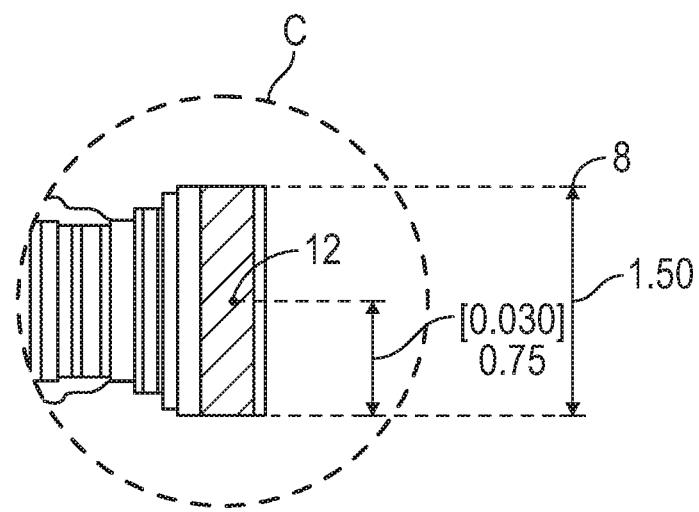
FIG. 11 is an enlarged front view of a capsular tension ring, according to some embodiments.

As seen in FIG. 11, for example, each of the eyelets 11 can emerge from an eyelet hole 12. FIG. 11 shows a detailed view of the second end 8. In this embodiment, the end has a vertical height (or axial thickness) of 1.50 millimeters. The eyelet hole 12 is shown equidistantly in the end of the ring.

Figure 12:
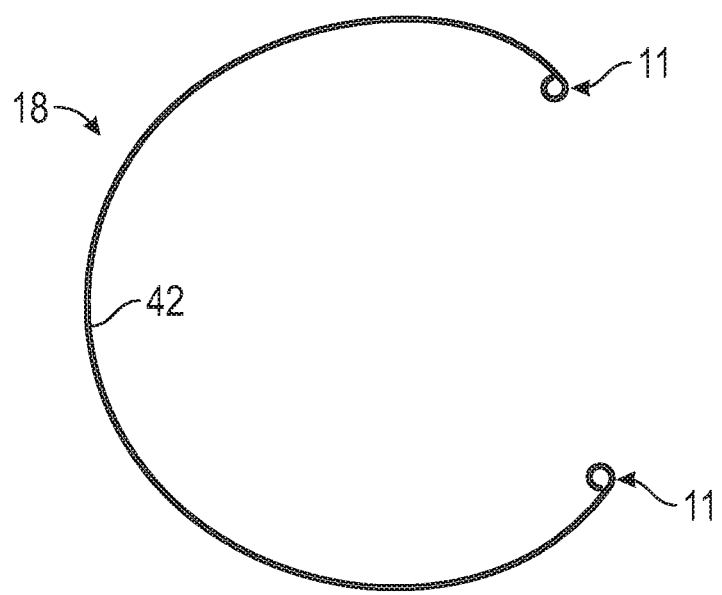
FIG. 12 is a plan view of an inner section of a capsular tension ring, according to some embodiments.

FIG. 12 shows an example of the inner section 18 with eyelets 11 and without outer section 17. This example is a nitinol inner wire section. The nitinol inner wire section has an annular or arcuate portion 42 connecting the eyelets 11 at opposing ends of the inner section wire section.

Figure 13A:
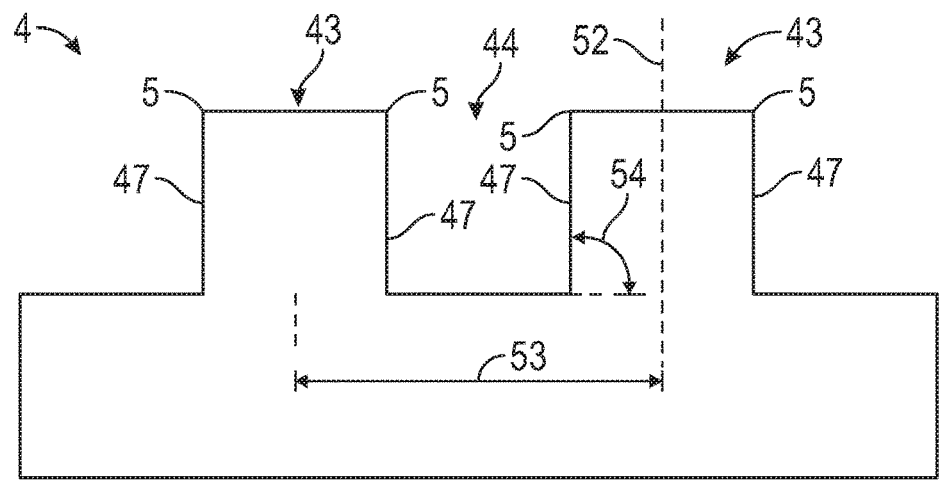
FIGS. 13A-13C are section views showing features of a capsular tension ring, according to some embodiments.
Figure 13B:
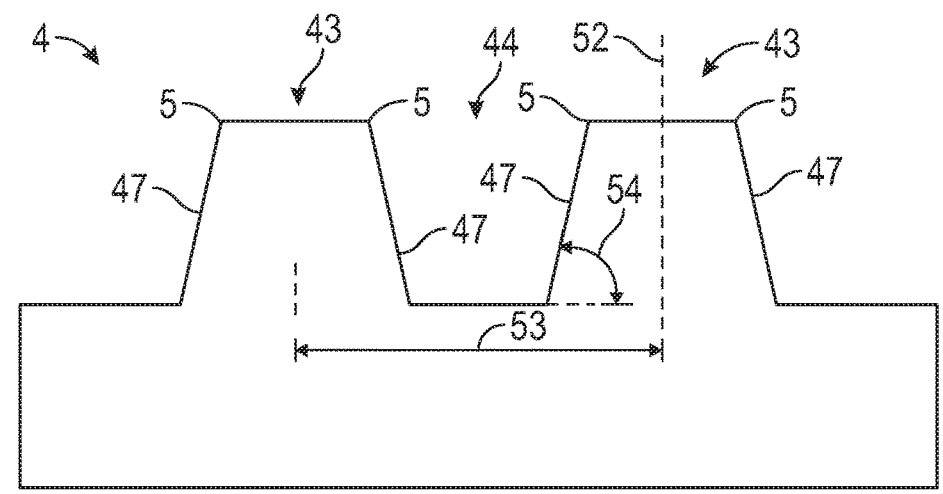
Figure 13C:
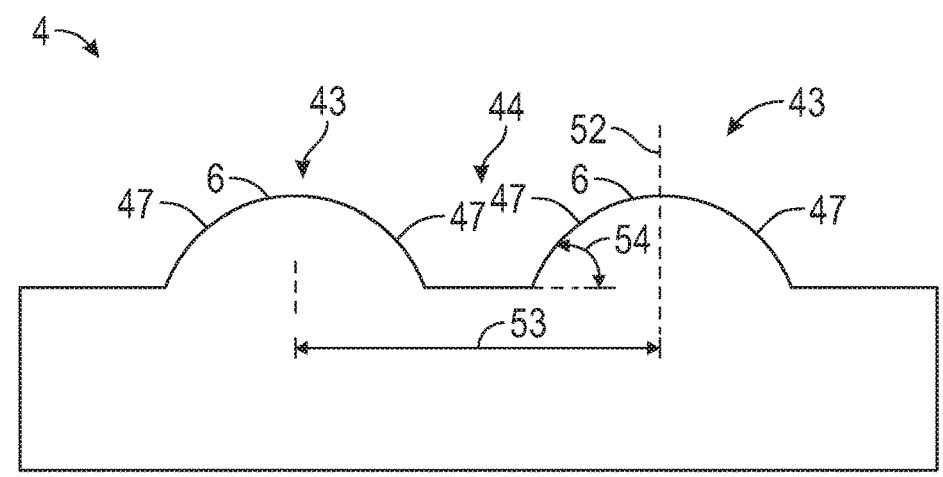

FIGS. 13A-13C show examples of features 4 that can be employed on the capsular tension ring 1 on the inner surface 3 and/or outer surface 2. These figures are a schematic representation of a cross section of the features 4 taken along a plane that intersects the outer section 17 in a direction perpendicular to the central axis 38.

FIG. 13A is a schematic representation of the features 4 shown in FIGS. 1-3, which include ridges 43 and valleys 44 having sharp edge 5. As seen in FIG. 13A, the opposing sides 47 can extend parallel to each other and be sloped at an angle 54 of approximately 90 degrees. The ridges 43 have a generally rectangular profile.

FIG. 13B is a schematic representation of another example of the features 4. In this example, the features 4 have a generally trapezoidal profile. The features 4 include ridges 43 and valleys 44 in which opposing sides 47 of each ridge converge towards each other, and in which the opposing sides are sloped at an angle less than 90 degrees.

FIG. 13C is a schematic representation of another example of the features 4. In this example, the features 4 have a generally curved profile. The features 4 include ridges 43 and valleys 44 in which opposing sides 47 of each ridge converge towards each other, and in which the opposing sides are sloped at an angle less than 90 degrees.

In each of the examples shown in FIGS. 13A-13C, each of the features 4 are shown as radially symmetric. In particular, the ridges 43 are symmetric about a radial line segment 52 that extends from the central axis 38 through the ridges 43 and bisects the ridges 43 (central axis 38 not shown in this figure). According to some embodiments, radially symmetric arrangements such as those shown in FIGS. 13A-13C can permit bi-directional rotational of an interfacing device such as an intraocular lens or haptic of an intraocular lens as the interfacing device slides along the ridges 43 in either rotational direction (e.g., clockwise or counterclockwise) with substantially equal levels of resistance in either direction.

In each of the examples shown in FIGS. 13A-13C, each of the features 4 are also shown with a slope angle 54 with respect to the surface from which that feature protrudes. According to some embodiments, this slope angle 54 can determine a degree of rotational resistance to rotation of an interfacing device as the interfacing device slides along the features. In this case, a greater angle can provide greater rotational resistance while a lesser angle can provide lesser rotational resistance. In these illustrated examples, the rectangular ridges shown in FIG. 13A have the greatest slope angle 54 at an angle of approximately 90 degrees and can provide the greatest rotational resistance out of these examples, followed by the trapezoidal ridges shown in FIG. 13B which have a slope angle 54 of less than 90 degrees, followed by the curved ridges shown in FIG. 13C which have the lowest slope angle 54 and can provide the least amount of rotational resistance out of these examples. It is contemplated that a variety of slope angles 54 can be suitably used in various implementations. According to some embodiments, the slope angle can be between 30 degrees and 100 degrees. It is also contemplated that bi-directional rotation of the interfacing device can be achieved in some cases without a radially symmetric arrangement, for example, if the slope angle 54 for the two opposing sides 47 differ from one another but are both less than 90 degrees.

In each of the examples shown in FIGS. 13A-13C, the ridges 43 shown also form adjacent pairs of ridges that can be spaced apart from each other at a pitch 53. This pitch 53 can determine the angle subtended 46 from the central axis 38 by the adjacent pair or by an arc extending between the adjacent pair of ridges. According to some embodiments, the pitch 53 can determine a rotational precision for step wise rotation of the interfacing device as it slides along the ridges. Accordingly, the pitch 53 can be selected to correspond to any of the subtended angles described herein.

Figure 14A:
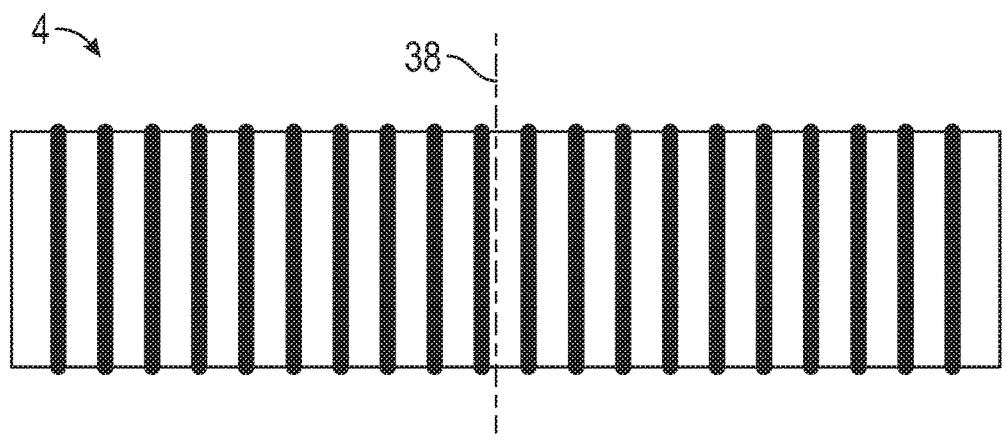
FIGS. 14A-14C are side views showing features of a capsular tension ring, according to some embodiments.
Figure 14B:
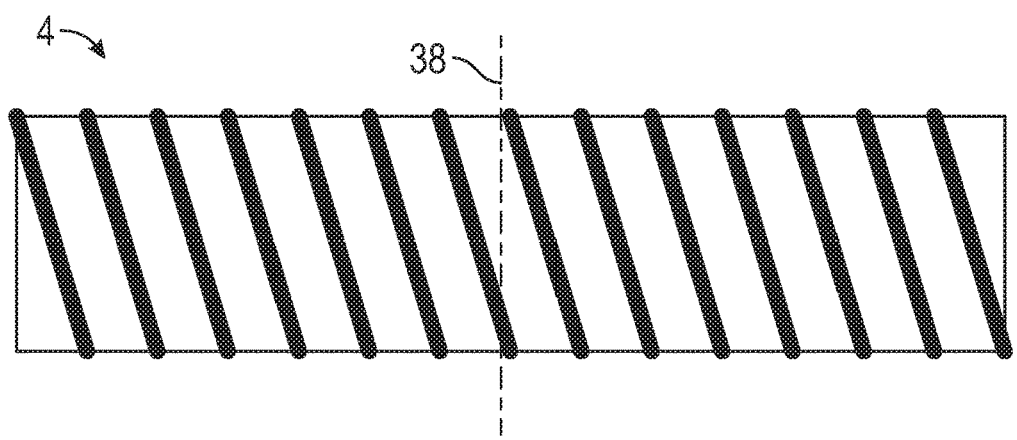
Figure 14C:
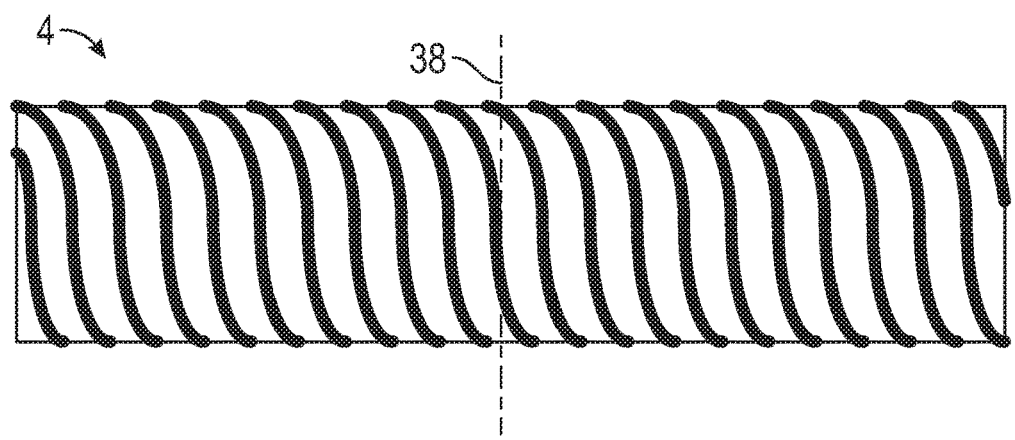

FIGS. 14A-14C show further examples of features 4, according to some embodiments. FIGS. 14A-14C show the features from a side view, e.g., when the features 4 are viewed in a direction normal to the inner surface 3 (for features protruding from the inner surface) or the outer surface 2 (for features protruding from the outer surface). FIGS. 14A-14C each show examples in which the features 4 are implemented as parallel polygon features arranged as a pattern of parallel ridges (black lines) and valleys (white spaces between black lines). As seen for example in FIG. 14A, the ridges can be arranged to extend substantially straight in the axial direction and substantially parallel to central axis 38. As seen for example in FIG. 14B, the ridges can be arranged to extend at an angle in the axial direction and at a non-zero angled to central axis 38 (e.g., similar to the teeth of a helical gear). As seen for example in FIG. 14C, the ridges can be arranged to with curved geometry with a series of parallel curves (e.g., similar to the teeth of a screw gear). Any one of these arrangements shown in FIGS. 14A-14C can be configured in accordance with any one of the arrangements shown in FIGS. 13A-13C, for example.

It will be appreciated that the shapes and arrangements shown in FIGS. 13-14 are just some examples that can be employed in the capsular tension ring 1, and it is contemplated that numerous other shapes, arrangements, and dimensions can be employed. Further, while the above examples explain some exemplary considerations or technical effects that can be achieved by the various parameters, it is contemplated that other principles of operation or effects can be utilized in the capsular tension ring 1 without being tied to these particular principles.

Figure 15:
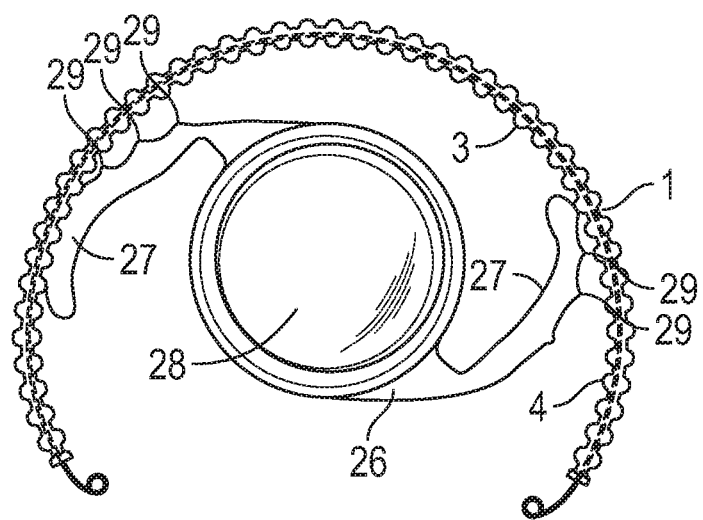
FIG. 15 is a plan view of a capsular tension ring and an intraocular lens in a relaxed configuration, according to some embodiments.

FIG. 15 shows an ophthalmic system including capsular tension ring 1 arranged around an interfacing device such as an intraocular lens 26. As seen in FIG. 15, the intraocular lens 26 have a central optic 28 (also referred to herein as an "optical element"), such as a toric or other type of artificial lens, and one or more haptics 27 (also referred to herein as "haptic elements") extending radially outwardly from the central optic 28 and attached or coupled to the central optic 28 to provide structural support. In this particular example, the haptics 27 are implemented as a pair of arms in which each arm spirals outwardly from the central optic 28, although it is contemplated that any other suitable haptics may be used.

The haptic(s) 27 are configured to mate with the annular inner surface 3 of the capsular tension ring 1. For example, the haptic(s) can each include one or more mating features 29 on an outer surface thereof. The mating features 29 on the haptic(s) 27 can be configured to interleave with or interact with features 4 of the capsular tension ring 1, and can include any complementary features to the features 4 of the capsular tension ring 1. According to some embodiments, the mating features 29 can include protrusions, ridges and valleys, and raised polygon features, or raised parallel polygon features that are configured to slidingly engage with corresponding features 4 of the capsular tension ring 1.

Figure 16:
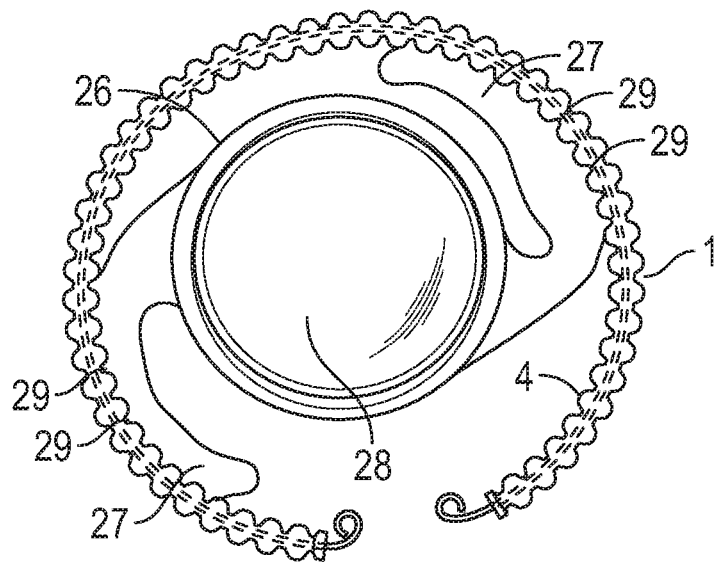
FIG. 16 is a plan view of a capsular tension ring and an intraocular lens in a compressed configuration, according to some embodiments.

FIG. 15 shows the capsular tension ring 1 in a relaxed configuration around the intraocular lens 26 such that the intraocular lens is not fully secured or engaged with the capsular tension ring 1. FIG. 16 shows the capsular tension ring 1 in a compressed configuration such that the mating features 29 on the haptic(s) 27 are engaged with and interleaved with the features 4 of the capsular tension ring, and such that the intraocular lens 26 is secured substantially coaxially within the ring. According to some embodiments, the mating features 29 of the haptic 27 can be slidingly engaged with the features 4 of the capsular tension ring 1 when in an engaged configuration like that shown in FIG. 16. The features can resist undesired rotation of the intraocular lens in the absence of any external force, while permitting bi-directional rotation about the central axis (e.g., clockwise and counterclockwise) upon application of external force to the intraocular lens 26. This can be accomplished using, for example, radially symmetric features such as those described above, or any other suitable features that allow for such sliding engagement.

Figure 17:
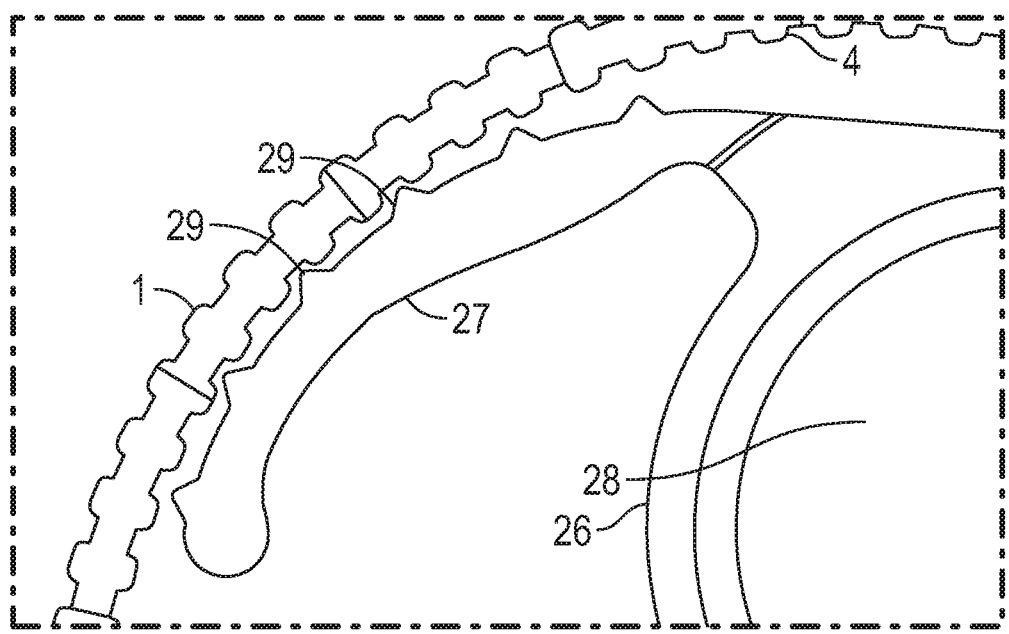
FIG. 17 is an enlarged view of a capsular tension ring mated with a haptic of an intraocular lens, according to some embodiments.

FIG. 17 shows an enlarged view of mating between features 4 of the capsular tension ring 1 and mating features 29 of the haptic 27. As seen for example in FIG. 17, the mating features 29 of the haptic 27 do not necessarily need to mate with the features of the ring with 1:1 correspondence. In this example, the mating features 29 have a pitch that is about twice the pitch of the features 4 of the ring, such that the features 4 of the ring mate with the mating features of the haptic with 2:1 correspondence. It is contemplated that a variety of relative pitches and mating correspondences may be used in various implementations. For example, according to some embodiments the mating features of the haptic can have a pitch that is substantially equal to the pitch of the features on the ring so that the features of the ring mate with the mating features of the haptic with 1:1 correspondence. According to some embodiments, the mating features of the haptic can have a pitch that is approximately double the pitch of the features on the ring so that the features of the ring mate with the mating features of the haptic with 2:1 correspondence. According to some embodiments, the mating features of the haptic can have a pitch that is approximately triple the pitch of the features on the ring so that the features of the ring mate with the mating features of the haptic with 3:1 correspondence. It is also contemplated that other arrangements may be used.

Figure 18:
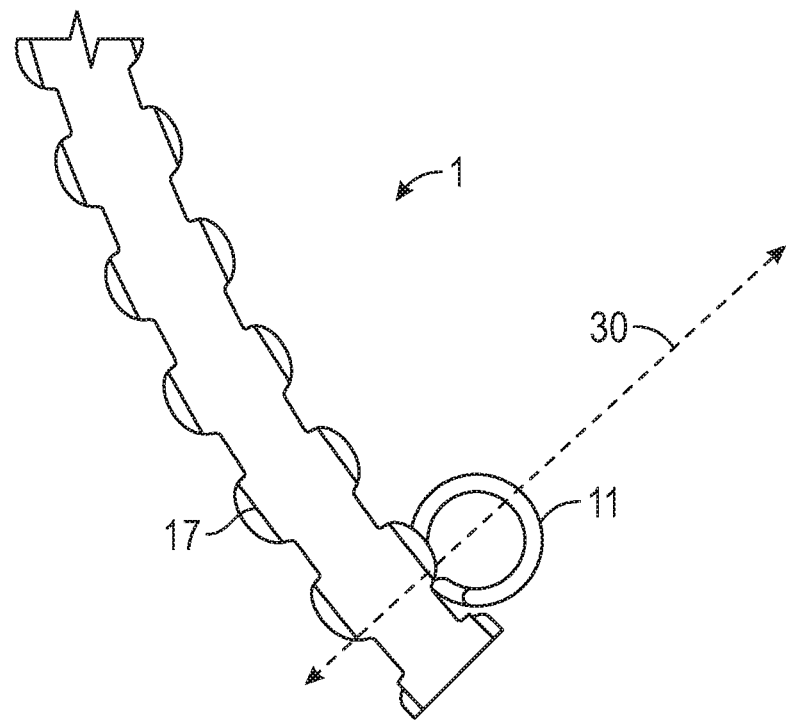
FIG. 18 is an enlarged view of an end of a capsular tension ring, according to some embodiments.

FIG. 18 shows an end of capsular tension ring 1, according to some embodiments. As seen in FIG. 18, the capsular tension ring 1 can include outer section 17 and an eyelet 11 extending from the outer section 17 so that it is exposed. The eyelet 11 can be attached to or be a part of inner section 18, which can be enveloped or covered by the outer section 17. As seen in FIG. 18, the outer section 17 can radially overlap with the eyelet 11, i.e., overlap with the eyelet 11 in the radial direction 30. In this case, a radial line segment originating from the central axis 38 and drawing radially outward through the outer section 17 will also intersect with the eyelet 11. This contrasts with the eyelets 11 shown in FIG. 1, for example, where the eyelets 11 and the outer section 17 do no radially overlap. According to some embodiments, such a radially overlapping arrangement may be useful to, for example, facilitate assembly or loading of the capsular tension ring 1 into an inserter device by reducing a tendency of the outer section to catch onto components of the inserter device as it is drawn in. In this example, the radially overlapping arrangement is achieved by having the eyelet 11 extend radially inwardly from the outer section 17 such that a portion of the outer section is radially outside of the inner section. It is contemplated that the capsular tension ring 1 can otherwise include any one or more of the aspects described above, including, for example, a wire inner section and an overmolded outer material section, for example.

4. Device Implantation

Some embodiments relate to a capsular tension ring for insertion into an ocular lens capsule to apply outward pressure in the area of the equatorial region, the capsular tension ring comprising an inner section 18 and an outer ring section 17, said inner section 18 having: a central fixation element; two arcuate arms (9 and 10) extending generally oppositely from the fixation element, said arms forming an arc to engage along the equatorial region of the capsule, said fixation element and arms being constructed; and outer section 17 enveloping said inner section 18. In some embodiments, said outer section 17 has: a vertical profile of at least 1.0 millimeters and horizontal profile of at least 150 micrometers. In some embodiments, said central fixation element adapted to be received by an insertion device. In some embodiments, said capsular tension ring arms (9 and 10) are arranged relatively to be loaded into the insertion device 25 by pulling on the central fixation element and thereby draw the arms into the insertion device 25 together, followed by discharge of the arcuate arms (9 and 10) together from the device into the capsule. In some embodiments, said fixation element and the arms are coplanar. In some embodiments, said ring further includes a stem section between the fixation element and the arms. In some embodiments, said arms are coplanar and the fixation element is offset out of the plane of the arms when deployed in a capsule. In some embodiments, said fixation element is an eyelet. In some embodiments, said fixation element is a groove formed between adjacent ends of the arms. In some embodiments, said inner section is made from nitinol. In some embodiments, said outer section is made from polymer materials that allows for absorption or incorporation of drugs for slow release. In some embodiments, said outer section 17 is overmolded upon said inner section. In some embodiments, said outer section has at least one distinct edge. In some embodiments, said distinct edge comprises a sharp edge 5. In some embodiments, said outer section has at least one curved edge 6. In some embodiments, said outer section has vertical features 13. In some embodiments, said outer section vertical features comprise outer ring surface vertical features. In some embodiments, said outer section vertical features comprises inner ring surface vertical features 13. In some embodiments, said ring provides rotational stability to the subsequently implanted intraocular lens. In some embodiments, said features are produced by etching. In some embodiments, the device is folded inside the capsular sac in a plane oblique or transverse to the general plane of the ocular lens capsule before it is released, thereby enabling the device to take up its place in the equatorial region without risk of lesion of the sac or of tearing of the zonules, thanks to the damping effect of the flexible material junction, which reduces the impact of the segment with the tissue of the capsular sac.

The diameter of the capsular tension ring may be selected so that, once implanted, it is slightly compressed against the equatorial region of the capsular sac. This compression has the effect of closing the capsular tension ring by moving its ends toward each other, the first end 7 passing outside the second end 8 and thus forming a very small step at the overlap of the ends 7 and 8. The resulting discontinuity is minimized by the small thickness and the inherent flexibility of the first end 7, which tends to be crushed radially between the end 8 and the capsular tissue at the level of the equator. Afterwards, in the post-operative period, the capsular sac may shrink, by about 0.5 mm to 1.5 mm in diameter, the consequence of which is to increase the overlapping length.

After implanting the capsular tension ring, the surgeon may position an intraocular lens 26 inside the ring. The haptic elements 27 can be C-shaped, J-shaped or flat, with or without an aperture, and there can be two or three of them, for example. Each is in contact with or bears against the cylindrical interior surface of the main portion of the annular body. Some intraocular lens 26 have three haptic elements 27 with a large aperture extending from the periphery of the optic 28 and forming an assembly with the capsular tension ring 1. The ring 1 therefore advantageously serves also to center and locate the intraocular lens 26 in the capsular sac. The axial width of the interior surface may provide a good bearing surface for the haptic elements of the intraocular implant.

A ring of the above kind has the advantage of maintaining its diameter despite shrinkage of the capsular sac. The raised features, vertical and horizontal features, and in some cases at least one sharp edge provide an excellent barrier to cellular migration. The inner section 18 comprises rigid material and the overmolded outer section 17 has said features.

In one embodiment, implanting the ring 1 may be followed by implanting the intraocular lens 26 in accordance with the standard practice using forceps or an injector. The haptic elements 27 of the intraocular lens are in contact with or bear against the annular interior surface of the main portion of the ring.

According to some embodiments, a method of treatment can involve, implanting a capsular tension ring in an eye, the capsular tension ring comprising an inner surface having a plurality of features. The method can further involve rotating a haptic element of an intraocular lens along the plurality of features in a first rotational direction. The method can further involve rotating the haptic element of the intraocular lens along the plurality of features in a second rotational direction opposite to the first rotational direction. According to some embodiments, the rotation in the first and second directions can be performed during an implantation procedure to rotationally position, for example, a toric intraocular lens with respect to the eye. According to some embodiments, the method can further involve further rotating the intraocular lens with respect to the eye in a subsequent procedure (e.g., after an initial post-operative period). This may be useful to, for example, prevent or mitigate tissue ingrowth into the haptics of the intraocular lens.

Some embodiments of the capsular tension ring may be impregnated beforehand with an anti-proliferation product. Some embodiments of the capsular tension ring may have micropatterned anti-proliferation surfaces as described in U.S. patent application Ser. No. 14/396,941, the disclosure of which is hereby incorporated by reference in its entirety for all purposes. The teachings of the present disclosure are not limited to the embodiments described or to the preferred materials, but to the contrary encompass all variants of structures, configurations and materials that are compatible with the subject matter of the present disclosure.

The present disclosure contemplates embodiments comprising devices and methods for stabilization of an ocular lens capsule and preventing artificial intraocular lens implant rotation post cataract surgery, are well adapted to attain the ends and advantages mentioned as well as those that are inherent therein. The particular embodiments disclosed above are illustrative only, as the teachings of present disclosure may be modified and practiced in different but equivalent manners apparent to those skilled in the art having the benefit of the present disclosure. It is therefore evident that the particular illustrative embodiments disclosed herein may be altered or modified and all such variations are considered within the scope and spirit of the present disclosure. Although the subject technology has been described with reference to these particular embodiments, other embodiments can achieve the same results. The entire disclosures of all applications, patents, and publications cited above, and of the corresponding application are hereby incorporated by reference.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. Any accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A capsular tension ring configured to be anchored in place within a lens capsule of an eye, the capsular tension ring comprising:
   an inner ring section; and
   an outer ring section at least partially enveloping the inner ring section, the outer ring section comprising:
      an outer ring surface;
      an inner ring surface, the outer ring surface and the inner ring surface each being annular surfaces extending about a central axis forming a geometric center of the capsular tension ring, wherein the inner ring section is disposed between the outer ring surface and the inner ring surface relative to the geometric center;
      a plurality of raised features disposed on the outer ring surface and extending outwardly of the geometric center from the outer ring surface; and a plurality of raised features disposed on the inner ring surface and extending inwardly toward the geometric center from the inner ring surface,
wherein each of the raised polygon features is radially symmetric, and
wherein the plurality of raised features disposed on the outer ring surface are configured to secure the capsular tension ring in place within the lens capsule of the eye.

2. The capsular tension ring of claim 1, wherein the inner ring section is made from a wire and the outer ring section is made from an elastic material molded or deposited over the wire.

3. The capsular tension ring of claim 2, wherein the wire is a nitinol wire and the elastic material is silicone.

4. The capsular tension ring of claim 1, wherein each of the raised features protrudes from the inner ring surface towards a geometric center of the capsular tension ring, and wherein each of the raised features has opposing sides extending substantially parallel to each other towards the geometric center.

5. The capsular tension ring of claim 1, each of the raised features on the inner ring surface has opposing sides that curve towards each other.

6. The capsular tension ring of claim 1, wherein an angle subtended from a central axis of the inner ring section by an adjacent pair of the raised features on the inner ring surface is between 0.5 degrees and 10 degrees.

7. The capsular tension ring of claim 6, wherein the angle subtended is between 0.5 degrees and 5 degrees.

8. The capsular tension ring of claim 7, wherein the angle subtended is between 0.5 degrees and 3 degrees.

9. The capsular tension ring of claim 1, wherein the sides of each of the raised features are sloped from a corresponding inner or outer ring surface at an angle of between 30 degrees to 100 degrees.

10. The capsular tension ring of claim 1, wherein each of the raised features has opposing sides that extend substantially parallel to each other.

11. The capsular tension ring of claim 1, wherein each of the raised features has opposing sides that converge towards each other in a radial inward direction.

12. The capsular tension ring of claim 1, wherein each of the raised features has a rectangular profile.

13. A capsular tension ring configured to be anchored in place within a lens capsule of an eye, the capsular tension ring comprising:
an inner ring annular surface extending circumferentially about a geometric center of the capsular tension ring;
an outer ring annular surface extending circumferentially about the geometric center of the capsular tension ring and concentric to the inner ring annular surface, wherein a first width between the inner ring annular surface and the outer ring annular surface is the thinnest section of the capsular tension ring;
a first end having a first eyelet;
a second end having a second eyelet, wherein the first and second ends are movable towards each other upon compression of the capsular tension ring;
a plurality of raised features disposed on the outer ring annular surface, each protruding away from the geometric center from the outer ring annular surface, and configured to secure the capsular tension ring in place within the lens capsule of the eye; and
a plurality of raised features disposed on the inner ring annular surface, each protruding towards the geometric center of the capsular tension ring from the inner ring annular surface, wherein a second width between peaks of opposing raised features disposed on the inner and outer ring annular surfaces is the thickest section of the capsular tension ring, and wherein each of the raised features is radially symmetric.

14. The capsular tension ring of claim 13, wherein each of the raised features on the inner ring annular surface has opposing sides that curve towards each other.

15. The capsular tension ring of claim 13, wherein each of the raised features has opposing sides that are each sloped at an angle of less than 90 degrees.

16. The capsular tension ring of claim 13, wherein an angle subtended from the geometric center by an adjacent pair of the raised features on the inner ring annular surface is between 0.5 degrees and 10 degrees.

17. The capsular tension ring of claim 16, wherein the angle subtended is between 0.5 degrees and 5 degrees.

18. The capsular tension ring of claim 16, wherein the angle subtended is between 0.5 degrees and 3 degrees.

19. The capsular tension ring of claim 13, wherein each of the raised features has opposing sides that converge towards each other in a radial inward direction.

20. A capsular tension ring comprising:
an open ring structure configured to circumferentially fit within a lens capsule of an eye, the open ring structure comprising:
an outer ring surface;
an inner ring surface, wherein the outer ring surface and the inner ring surface are concentric annular surfaces extending about a geometric center of the capsular tension ring, the outer ring surface and the inner ring surface disposed apart at a constant width;
a plurality of raised features disposed on the outer ring surface and extending outwardly of the geometric center from the outer ring surface; and
a plurality of raised features disposed on the inner ring surface and extending inwardly toward the geometric center from the inner ring surface, wherein the plurality of raised features disposed on the outer ring surface are configured to secure the capsular tension ring in place within the lens capsule of the eye.

21. The capsular tension ring of claim 20, wherein each of the raised features has opposing sides that curve towards each other.

22. The capsular tension ring of claim 20, wherein an angle subtended from a geometric center of the open ring structure by an adjacent pair of the raised features is between 0.5 degrees and 10 degrees.

23. The capsular tension ring of claim 20, wherein the open ring structure further comprises a first end and a second end, wherein at least one of the first end or the second end comprises an eyelet.

24. A capsular tension ring configured to be anchored in place within a lens capsule of an eye, the capsular tension ring comprising:
an inner ring surface extending circumferentially about a geometric center of the capsular tension ring;
an outer ring surface extending circumferentially about the geometric center of the capsular tension ring at a constant distance from the inner ring surface;
a first end having a first eyelet;
a second end having a second eyelet, wherein the first and second ends are movable towards each other upon compression of the capsular tension ring; and
a plurality of raised features on the outer ring surface and on the inner ring surface, wherein each of the raised features on the inner ring surface protrudes towards the geometric center from the inner ring surface and each of the raised features on the outer ring surface protrudes away from the geometric center, and wherein the plurality of raised features on the outer ring surface are configured to secure the capsular tension ring in place within the lens capsule of the eye.

25. The capsular tension ring of claim 24, wherein each of the raised features on the inner ring surface has opposing sides that curve towards each other.

26. The capsular tension ring of claim 24, wherein an angle subtended from the geometric center by an adjacent pair of the raised features on the inner ring surface is between 0.5 degrees and 10 degrees.

27. The capsular tension ring of claim 20, wherein each of the raised features has opposing sides that converge towards each other in a radial inward direction.

28. The capsular tension ring of claim 20, wherein each of the raised features has opposing sides, each opposing side sloped at an angle of less than 90 degrees.

29. The capsular tension ring of claim 24, wherein each of the raised features has opposing sides that converge towards each other in a radial inward direction.

30. The capsular tension ring of claim 24, wherein each of the raised features has opposing sides, each opposing side sloped at an angle of less than 90 degrees.

* * * * *

UNITED STATES PATENT AND TRADEMARK OFFICE
CERTIFICATE OF CORRECTION

PATENT NO.      : 10,561,493 B2
APPLICATION NO. : 16/228623
DATED           : February 18, 2020
INVENTOR(S)     : Malik Y. Kahook It is certified that error appears in the above-identified patent and that said Letters Patent is hereby corrected as shown below:

In the Claims

Column 21, Line 4 (Claim 1): Replace "raised polygon features" with --raised features--.

Signed and Sealed this
Seventh Day of April, 2020

Andrei Iancu
*Director of the United States Patent and Trademark Office*